(12) United States Patent
Kawa

(10) Patent No.: US 11,154,489 B1
(45) Date of Patent: Oct. 26, 2021

(54) ANTI-AGING HAIR TREATMENT

(71) Applicant: Ino Beauty, Inc., Miami, FL (US)

(72) Inventor: Nour Kawa, Miami, FL (US)

( * ) Notice: Subject to any disclaimer, the term of this patent is extended or adjusted under 35 U.S.C. 154(b) by 294 days.

(21) Appl. No.: 16/294,684

(22) Filed: Mar. 6, 2019

Related U.S. Application Data

(62) Division of application No. 15/096,247, filed on Apr. 11, 2016, now Pat. No. 10,278,915.

(51) Int. Cl.

| | |
|---|---|
| *A61K 8/898* | (2006.01) |
| *A61K 8/9794* | (2017.01) |
| *A61K 8/9789* | (2017.01) |
| *A61K 8/34* | (2006.01) |
| *A61K 8/368* | (2006.01) |
| *A61K 8/37* | (2006.01) |
| *A61K 8/41* | (2006.01) |
| *A61K 8/44* | (2006.01) |
| *A61K 8/49* | (2006.01) |
| *A61K 8/64* | (2006.01) |
| *A61K 8/891* | (2006.01) |
| *A61Q 5/00* | (2006.01) |
| *A61Q 5/02* | (2006.01) |
| *A61Q 5/12* | (2006.01) |
| *A61K 8/86* | (2006.01) |

(52) U.S. Cl.
CPC .............. *A61K 8/898* (2013.01); *A61K 8/342* (2013.01); *A61K 8/345* (2013.01); *A61K 8/368* (2013.01); *A61K 8/37* (2013.01); *A61K 8/416* (2013.01); *A61K 8/44* (2013.01); *A61K 8/498* (2013.01); *A61K 8/4993* (2013.01); *A61K 8/64* (2013.01); *A61K 8/86* (2013.01); *A61K 8/891* (2013.01); *A61K 8/9789* (2017.08); *A61K 8/9794* (2017.08); *A61Q 5/002* (2013.01); *A61Q 5/02* (2013.01); *A61Q 5/12* (2013.01)

(58) Field of Classification Search
CPC .... A61K 8/898; A61K 8/9794; A61K 8/9789; A61K 8/342; A61K 8/345; A61K 8/368; A61K 8/37; A61K 8/416; A61K 8/44; A61K 8/498; A61K 8/4993; A61K 8/64; A61K 8/86; A61K 8/891; A61Q 5/002; A61Q 5/02; A61Q 5/12
See application file for complete search history.

(56) References Cited

U.S. PATENT DOCUMENTS 7,989,599 B2    8/2011  Suzuki et al.
8,048,920 B2 *  11/2011  Joerger ................. A61K 36/02
                                                                  514/546

* cited by examiner

*Primary Examiner* — Jianfeng Song
(74) *Attorney, Agent, or Firm* — Sanchelima & Associates, P.A.; Christian Sanchelima; Jesus Sanchelima

(57) ABSTRACT

A hair strengthening, nourishment, and growth composition and method of application that can be used in the form of a shampoo, conditioner, and a serum.

3 Claims, No Drawings

ANTI-AGING HAIR TREATMENT

OTHER RELATED APPLICATIONS

The present application is a divisional patent application and claims the benefit of the priority date of U.S. non-provisional patent application Ser. No. 15/096,247 filed on Apr. 11, 2016, which is hereby incorporated by reference.

BACKGROUND OF THE INVENTION

Field of the Invention

The present invention relates to a hair, follicle and scalp composition and application method and, more particularly, to a composition that can be applied in a shampoo, conditioner and serum for stimulating hair follicles and neutralizing the scalp to stimulate longer, stronger, healthier, fuller looking hair. The composition strengthens and nurtures existing hair and many experience the appearance of fullness, thickness and growth.

Description of the Related Art

Several compositions for hair treatments have been designed in the past. None of them, however, include a composition that focuses on the health of the scalp, neutralizing the PH levels, providing the necessary ingredients to stimulate growth topically and to penetrate deeper into the scalp, while providing ingredients the stimulate blood vessels, provide protein and plant based nourishment and minimize inflammation.

Applicant believes that a related reference corresponds to U.S. Pat. No. 7,989,599 issued to National Institute of Advanced Ind Science and Tech AIST Toyo Boseki KK for an activator including biosurfactant as active ingredient, mannosyl erythritol lipid, and production method thereof.

However, it differs from the present invention because it does not teach or motivate one of ordinary skill in the art to combine the ingredients and combinations of the present formulation to provide as effective of a composition to promote the anti-aging of hair.

Other documents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a composition that increases healing and suppresses free radical development on the skin and/or scalp of the user.

It is another object of this invention to provide a composition that repairs and prevents ultraviolet damage, damage caused by excessive styling or chemical treatments.

It is another object of this invention to enhance the shine of a user's hair.

It is still another object of the present invention to provide moisture and nourishment to the hair.

It is yet another object of the present invention to provide stimulation to the hair follicles.

It is still another object of the present invention to stabilize the PH level of a user's scalp.

It is another object of the present invention to boost proteins linked to stem cell functions to promote hair growth.

It is still another object of the present invention to reduce split ends.

It is another object of the present invention to promote blood flow to the scalp.

It is yet another object of the present invention to facilitate the communication of cells.

It is yet another object of the invention to minimize the detrimental hair loss effects of Dihydrotestoterone.

It is still another object of the present invention to induce anti-inflammatory effects.

It is another object of the invention to prolong the life of existing hair.

It is another object of the invention to prevent excessive shedding, hair loss, increase hair density and volume, and activate dermal papilla cells.

The present invention can help hair look thicker, fuller, healthier and stronger than existing products on the market. Namely, it works by stimulating the hair follicle in various stages on the surface, i.e. wake it up.

It also has ingredients that: promote more circulation, blood flow and larger blood vessels; penetrate deeper into the scalp and signal the follicle to grow healthy; counter inflammation; provide balance; nourish the follicle, scalp and hair; balance hormonal disruption; and calm inflammation.

The state of the art includes compositions that are not focused on the scalp health and growth. They are focused on forcing the hair follicle to get back in its active stage, e.g. Rogain®, Nioxin®. There are other options that focus on stimulating the hair follicle.

The present invention focuses on the health of the scalp, neutralizing the PH levels, providing the necessary ingredients to stimulate growth topically and deeper into the scalp. The present invention provides these benefits while including ingredients that provide moisture, nourishment and support.

It is yet another object of this invention to provide such a composition that is inexpensive to implement and maintain while retaining its effectiveness.

Further objects of the invention will be brought out in the following part of the specification, wherein detailed description is for the purpose of fully disclosing the invention without placing limitations thereon.

DETAILED DESCRIPTION OF THE EMBODIMENTS OF THE INVENTION

The composition can be included in a shampoo. This shampoo also works synergistically with the conditioner and serum. It helps prepare the hair to receive the conditioner and serum.

The core ingredients of the shampoo include:
    a. Acetyl Cysteine
    b. Alcohol
    c. Inositol
    d. Lactose
    e. Citric acid
    f. Milk Protein (*lactis* Proteinum)
    g. Panthenyl Ethyl Ether;
    h. *Serenoa;*
    i. Sodium Citrate;
    j. *Glycine soja* (soybean) Germ Extract
    k. Biotinoyl Tripeptide
    l. Oleanolic Acid
    m. Butylene Glycol
    n. PEG-40 Hydrogenated Castor Oil
    o. PPG-26-Buteth-26;

p. Arginine
q. Lactic Acid
r. Propanediol
s. *Scutellaria ba-icalensis* Root Extract;
t. Acetyl Methione
u. *Triticum vulgare* (wheat) Germ Extract;
v. Beeswax;
w. Behenyl Alcohol
x. *Butyrospermum parkii* (Shea Butter) Extract
y. Ethylhexylglycerin
z. Hydroxyethyl Behenamidopropyl Dimonium Chloride
aa. Phenoxyethanol
bb. *Pyrus malus* Extract;
cc. Caprylhydroxamic Acid
dd. Caprylyl Glycol
ee. Glycerin;
ff. Cetyl Betaine;
gg. *Citrullus colocynthis* Fruit Extract
hh. *Pisum sativum* (Pea) Peptide;
ii. Cocamidopropyl Betaine
jj. Sodium Cocoyl Isethionate
kk. Sodium;
ll. *Cuscuta reflexa* (Giant Dodder) Extract;
mm. *Eclipta alba* Extract;
nn. Hydrolyzed *quinoa;*
oo. Hydrolyzed Rice Protein;
pp. *serrulata* Fruit Extract;
qq. Polyquaternium 7;
rr. Purified Water;
ss. Apigenin;
tt. Sodium Lauroyl Methyl Isethionate by weight;
uu. Stearamidopropyl Dimethylamine; and
vv. *Leuconostoc*/Radish Root Ferment Filtrate.

The shampoo composition prevents accelerated hair loss with milk based bioactive signaling molecules using sulfur-rich amino acids. Also, this composition activates the stem cells by focusing on the surrounding connecting tissue. This composition also increases hair thickness and prevents functional disorders of the scalp and follicle cells;

Amodimethicone. C11-15 Pareth-7, Laureth-9, Trideceth-12 is a Paraben-free system and is used for the purposes of detangling.

Apigenin, lead to stimulation of follicle cell metabolism and lead to the slow down of hair loss.

*Scutellaria ba-icalensis* Root Extract, *Triticum vulgare* (wheat) Germ Extract. This combination stimulates hair growth and stimulates hair stem cells. It lengthens the anogen hair cycle while shortening the telogen (or hair death) cycle. Helps actually change a hair from the telogen hair cycle to the anogen hair cycle. Provides additional sugars to the follicles which helps increase cellular respiration. Increases ATP production required for hair growth, development and maintenance. Protects against oxidative stress by microchondria stimulation;

Beeswax, *Butyrospermum parkii* (Shea Butter) Extract, *Pyrus malus* Extract promotes hair growth;

Citric Acid is used as a natural preservative and PH adjuster;

*Citrullus colocynthis* Fruit Extra and *Pisum sativum* (Pea) Peptide stimulate hair growth, nourishes and moisturizes the hair follicle;

Hydrolyzed *quinoa* provides hair repair and protection—substantively and penetration. Provides gloss and shine enhancement, hair color protection, and curl definition;

Hydrolyzed Rice Protein increases the volume of the hair shaft;

*Leuconostoc*/Radish Root Ferment Filtrate and *serrulata* Fruit Extract stimulate hair growth, nourishes and moisturizes the hair follicle.

Panthenyl Hydroxypropyl Steardimonium Chloride functions as an aesthetic, moisturizes and prevents fly aways;

Polyquaternium 7 that reduces static and prevents fly aways;

The composition can also be effectively implemented in the following ranges by percent by weight in a shampoo comprising:
a. approximately 0.5-8% Acetyl Cysteine by weight;
b. approximately 0.5-8% Acetyl Methione by weight;
c. approximately 0.5-8% Alcohol by weight;
d. approximately 0.5-8% Citric acid by weight;
e. approximately 0.5-8% Inositol by weight;
f. approximately 0.5-8% Lactose by weight;
g. approximately 0.5-8% Milk Protein (*lactis* Proteinum) by weight;
h. approximately 0.5-8% Panthenyl Ethyl Ether by weight;
i. approximately 0.5-8% Sodium Citrate by weight;
j. approximately 0.1-18% Apigenin by weight;
k. approximately 0.1-18% Biotinoyl Tripeptide by weight;
l. approximately 0.1-18% Butylene Glycol by weight;
m. approximately 0.1-18% Oleanolic Acid by weight;
n. approximately 0.1-18% PEG-40 Hydrogenated Castor Oil by weight;
o. approximately 0.1-18% PPG-26-Buteth-26 by weight;
p. approximately 0.15-10% Arginine;
q. approximately 0.15-10% *Glycine soja* (soybean) Germ Extract by weight;
r. approximately 0.15-10% Lactic Acid by weight;
s. approximately 0.15-10% Propanediol by weight;
t. approximately 0.15-10% *Scutellaria ba-icalensis* Root Extract by weight;
u. approximately 0.15-10% *Triticum vulgare* (wheat) Germ Extract by weight;
v. approximately 0.01-8% Beeswax by weight;
w. approximately 0.01-8% Behenyl Alcohol by weight;
x. approximately 0.01-8% *Butyrospermum parkii* (Shea Butter) Extract by weight;
y. approximately 0.01-8% Ethylhexylglycerin by weight;
z. approximately 0.01-8% Hydroxyethyl Behenamidopropyl Dimonium Chloride by weight;
aa. approximately 0.01-8% Phenoxyethanol by weight;
bb. approximately 0.01-8% *Pyrus malus* Extract by weight;
cc. approximately 0.005-8% Caprylhydroxamic Acid by weight;
dd. approximately 0.005-8% Caprylyl Glycol by weight;
ee. approximately 0.005-8% Glycerin by weight;
ff. approximately 1-23% Cetyl Betaine by weight;
gg. approximately 0.0001-7% *Citrullus colocynthis* Fruit Extract by weight;
hh. approximately 0.0001-7% *Pisum sativum* (Pea) Peptide by weight;
ii. approximately 0.0001-7% *Serenoa* by weight;
jj. approximately 1-50% Cocamidopropyl Betaine;
kk. approximately 1-50% Sodium Cocoyl Isethionate by weight;
ll. approximately 1-50% Sodium Lauroyl Methyl Isethionate by weight;
mm. approximately 1-50% Sodium by weight;

nn. approximately 0.0001-7% *Cuscuta reflexa* (Giant Dodder) Extract by weight;
oo. approximately 0.0001-7% *Eclipta alba* Extract by weight;
pp. approximately 0.01-7% Hydrolyzed *quinoa* by weight;
qq. approximately 0.01-8% Hydrolyzed Rice Protein by weight;
rr. approximately 0.0001-7% *Leuconostoc*/Radish Root Ferment Filtrate by weight;
ss. approximately 0.0001-7% *serrulata* Fruit Extract by weight;
tt. approximately 0.2-5% Polyquaternium 7 by weight;
uu. approximately 1-60% Purified Water by weight;
vv. approximately 0.1-4% Stearamidopropyl Dimethylamine by weight.

The composition can also be effectively implemented in the following ranges by percent by weight in one embodiment of the shampoo comprising:
a. approximately 1-4% Acetyl Cysteine by weight;
b. approximately 1-4% Acetyl Methione by weight;
c. approximately 1-4% Alcohol by weight;
d. approximately 1-4% Inositol by weight;
e. approximately 1-4% Lactose by weight;
f. approximately 1-4% Milk Protein (*lactis* Proteinum) by weight;
g. approximately 1-4% Panthenyl Ethyl Ether by weight;
h. approximately 1-4% Sodium Citrate by weight;
i. approximately 0.5-6% Apigenin by weight;
j. approximately 0.5-6% Biotinoyl Tripeptide by weight;
k. approximately 0.5-6% Butylene Glycol by weight;
l. approximately 0.5-6% Oleanolic Acid by weight;
m. approximately 0.5-6% PEG-40 Hydrogenated Castor Oil by weight;
n. approximately 0.5-6% PPG-26-Buteth-26 by weight;
o. approximately 0.5-3% Arginine by weight;
p. approximately 0.5-3% *Glycine soja* (soybean) Germ Extract by weight;
q. approximately 0.5-3% Lactic Acid by weight;
r. approximately 0.5-3% Propanediol by weight;
s. approximately 0.5-3% *Scutellaria ba-icalensis* Root Extract by weight;
t. approximately 0.5-3% *Triticum vulgare* (wheat) Germ Extract by weight;
u. approximately 0.1-4% Beeswax by weight;
v. approximately 0.1-4% Behenyl Alcohol by weight;
w. approximately 0.1-4% *Butyrospermum parkii* (Shea Butter) Extract by weight;
x. approximately 0.1-4% Ethylhexylglycerin by weight;
y. approximately 0.1-4% Hydroxyethyl Behenamidopropyl Dimonium Chloride (by weight;
z. approximately 0.1-4% Phenoxyethanol by weight;
aa. approximately 0.1-4% *Pyrus malus* Extract by weight;
bb. approximately 0.005-4% Caprylhydroxamic Acid by weight;
cc. approximately 0.005-4% Caprylyl Glycol by weight;
dd. approximately 0.005-4% Glycerin by weight;
ee. approximately 2-12% Cetyl Betaine by weight;
ff. approximately 0.001-4% Citric Acid by weight;
gg. approximately 0.0001-7% *Citrullus colocynthis* Fruit Extract by weight;
hh. approximately 0.0001-7% *Pisum sativum* (Pea) Peptide by weight;
ii. approximately 0.0001-7% *Serenoa* by weight;
jj. approximately 18-41% Cocamidopropyl Betaine by weight;
kk. approximately 18-41% Sodium Cocoyl Isethionate by weight;
ll. approximately 18-41% Sodium Lauroyl Methyl Isethionate by weight;
mm. approximately 18-41% Sodium by weight;
nn. approximately 0.1-3% *Cuscuta reflexa* (Giant Dodder) Extract by weight;
oo. approximately 0.1-3% *Eclipta alba* Extract by weight;
pp. approximately 1-5% Hydrolyzed *quinoa* by weight;
qq. approximately 0.01-5% Hydrolyzed Rice Protein by weight;
rr. approximately 0.0001-7% *Leuconostoc*/Radish Root Ferment Filtrate by weight;
ss. approximately 0.0001-7% *serrulata* Fruit Extract by weight;
tt. approximately 1-4% Polyquaternium 7 by weight;
uu. approximately 1-60% Purified Water by weight; and
vv. approximately 0.5-3% Stearamidopropyl Dimethylamine by weight;

The core and secondary ingredients of the shampoo include:
a. Acetyl Cysteine;
b. Acetyl Methione;
c. Alcohol;
d. Citric acid;
e. Inositol;
f. Lactose;
g. Milk Protein (*lactis* Proteinum);
h. Panthenyl Ethyl Ether;
i. Sodium Citrate;
j. Acrylates/C10-30 Alkyl Acrylates Crosspolymer;
k. Amodimethicone;
l. C11-15 Pareth-7;
m. Laureth-9;
n. Trideceth-12;
o. Apigenin;
p. Biotinoyl Tripeptide;
q. Butylene Glycol;
r. Oleanolic Acid;
s. PEG-40 Hydrogenated Castor Oil;
t. PPG-26-Buteth-26;
u. Arginine;
v. *Glycine soja* (soybean) Germ Extract;
w. Lactic Acid;
x. Propanediol;
y. *Scutellaria ba-icalensis* Root Extract;
z. *Triticum vulgare* (wheat) Germ Extract;
aa. Beeswax;
bb. Behenyl Alcohol;
cc. *Butyrospermum parkii* (Shea Butter) Extract;
dd. Ethylhexylglycerin;
ee. Hydroxyethyl Behenamidopropyl Dimonium Chloride;
ff. Phenoxyethanol;
gg. *Pyrus malus* Extract;
hh. *Camellia sinensis* Leaf Extract;
ii. Caprylic/Capric Triglyceride;
jj. *Coffea arabica* (Coffee) Leaf/Seed Extract;
kk. *Cucumis melo* Cantalupensis Fruit Extract;
ll. *Eugenia caryophyllus* (Clove) Flower Extract;
mm. *Elettaria cardamomum* Seed Extract;
nn. *Jasminum officinale* (Jasmine) Flower/Leaf Extract;
oo. *Pyrus malus* Apple Fruit Extract;
pp. *Rosa damascena* Flower Extract;
qq. *Rubus fruticosus* (Blackberry) Fruit Extract;
rr. Caprylhydroxamic Acid;
ss. Caprylyl Glycol;

tt. Glycerin;
uu. Cetyl Betaine;
vv. *Citrullus colocynthis* Fruit Extract;
ww. *Pisum sativum* (Pea) Peptide (and) *Serenoa*;
xx. Glycol Distearate;
yy. Laureth-4;
zz. Cocamidopropyl Betaine;
aaa. Sodium Cocoyl Isethionate;
bbb. Sodium;
ccc. *Cuscuta reflexa* (Giant Dodder) Extract;
ddd. *Eclipta alba* Extract;
eee. Guar Hydroxypropyltrimonium Chloride;
fff. Hydrolyzed *quinoa*;
ggg. Hydrolyzed Rice Protein;
hhh. *Leuconostoc*/Radish Root Ferment Filtrate;
iii. *serrulata* Fruit Extract;
jjj. Methyl Oleoyl Taurate;
kkk. Panthenyl Hydroxypropyl Steardimonium Chloride;
lll. Polyquaternium 7;
mmm. Purified Water;
nnn. Sodium Lauroyl Methyl Isethionate; and
ooo. Stearamidopropyl Dimethylamine.

The shampoo can be implemented with the following ranges:
a. approximately 0.5-8% Acetyl Cysteine by weight;
b. approximately 0.5-8% Acetyl Methione by weight;
c. approximately 0.5-8% Alcohol by weight;
d. approximately 0.5-8% Inositol by weight;
e. approximately 0.5-8% Lactose by weight;
f. approximately 0.5-8% Milk Protein (*lactis* Proteinum) by weight;
g. approximately 0.5-8% Panthenyl Ethyl Ether by weight;
h. approximately 0.5-8% Sodium Citrate by weight; and
i. approximately 3-30% Acrylates/C10-30 Alkyl Acrylates Crosspolymer;
j. approximately 0.05-24% Amodimethicone by weight;
k. approximately 0.05-24% C11-15 Pareth-7 by weight;
l. approximately 0.0001-24% Glycerin by weight;
m. approximately 0.05-24% Laureth-9 by weight;
n. approximately 0.05-24% Trideceth-12 Paraben-free by weight;
o. approximately 0.1-18% Apigenin by weight;
p. approximately 0.1-18% Biotinoyl Tripeptide by weight;
q. approximately 0.1-18% Butylene Glycol by weight;
r. approximately 0.1-18% Oleanolic Acid by weight;
s. approximately 0.1-18% PEG-40 Hydrogenated Castor Oil by weight;
t. approximately 0.1-18% PPG-26-Buteth-26 by weight;
u. approximately 0.15-10% Arginine by weight;
v. approximately 0.15-10% *Glycine soja* (soybean) Germ Extract by weight;
w. approximately 0.15-10% Lactic Acid by weight;
x. approximately 0.15-10% Propanediol by weight;
y. approximately 0.15-10% *Scutellaria ba-icalensis* Root Extract by weight;
z. approximately 0.15-10% *Triticum vulgare* (wheat) Germ Extract by weight;
aa. approximately 0.01-8% Beeswax by weight;
bb. approximately 0.01-8% Behenyl Alcohol by weight;
cc. approximately 0.01-8% *Butyrospermum parkii* (Shea Butter) Extract by weight;
dd. approximately 0.01-8% Ethylhexylglycerin by weight;
ee. approximately 0.01-8% Hydroxyethyl Behenamidopropyl Dimonium Chloride by weight;
ff. approximately 0.01-8% Phenoxyethanol by weight;
gg. approximately 0.01-8% *Pyrus malus* Extract by weight;
hh. approximately 0.005-7% *Camellia sinensis* Leaf Extract by weight;
ii. approximately 0.005-7% Caprylic/Capric Triglyceride by weight;
jj. approximately 0.005-7% *Coffea arabica* (Coffee) Leaf/Seed Extract by weight;
kk. approximately 0.005-7% *Cucumis melo* Cantalupensis Fruit Extract by weight;
ll. approximately 0.005-7% *Eugenia caryophyllus* (Clove) Flower Extract by weight;
mm. approximately 0.005-7% *Elettaria cardamomum* Seed Extract by weight;
nn. approximately 0.005-7% *Jasminum officinale* (Jasmine) Flower/Leaf Extract by weight;
oo. approximately 0.005-7% *Pyrus malus* Apple Fruit Extract by weight;
pp. approximately 0.005-7% *Rosa damascena* Flower Extract by weight;
qq. approximately 0.005-7% *Rubus fruticosus* (Blackberry) Fruit Extract by weight;
rr. approximately 0.005-8% Caprylhydroxamic Acid by weight;
ss. approximately 0.005-8% Caprylyl Glycol by weight;
tt. approximately 1-23% Cetyl Betaine by weight;
uu. approximately 0.001-8% Citric Acid by weight;
vv. approximately 0.0001-7% *Citrullus colocynthis* Fruit Extract;
ww. approximately 0.0001-7% *Pisum sativum* (Pea) Peptide;
xx. approximately 0.0001-7% *Serenoa* by weight;
yy. approximately 1-8% Glycol Distearate;
zz. approximately 1-8% Laureth-4 by weight;
aaa. approximately 1-50% Cocamidopropyl Betaine by weight;
bbb. approximately 1-50% Sodium Cocoyl Isethionate by weight;
ccc. approximately 1-50% Sodium Lauroyl Methyl Isethionate by weight;
ddd. approximately 1-50% Sodium by weight,
eee. approximately 1-50% Methyl Oleoyl Taurate by weight;
fff. approximately 0.0001-7% *Cuscuta reflexa* (Giant Dodder) Extract by weight;
ggg. approximately 0.0001-7% *Eclipta alba* Extract by weight;
hhh. approximately 0.01-5% Guar Hydroxypropyltrimonium Chloride by weight;
iii. approximately 0.01-7% Hydrolyzed *quinoa* by weight;
jjj. approximately 0.01-8% Hydrolyzed Rice Protein by weight;
kkk. approximately 0.0001-7% *Leuconostoc*/Radish Root Ferment Filtrate by weight;
lll. approximately 0.0001-7% *serrulata* Fruit Extract by weight;
mmm. approximately 0.001-8% Panthenyl Hydroxypropyl Steardimonium Chloride by weight;
nnn. approximately 0.2-5% Polyquaternium 7 by weight;
ooo. approximately 1-60% Purified Water by weight; and
ppp. approximately 0.1-4% Stearamidopropyl Dimethylamine by weight.

In an alternate embodiment, the shampoo can be implemented using the following ranges:
a. approximately 1-4% Acetyl Cysteine by weight;
b. approximately 1-4% Acetyl Methione by weight;

c. approximately 1-4% Alcohol by weight;
d. approximately 1-4% Inositol by weight;
e. approximately 1-4% Lactose by weight;
f. approximately 1-4% Milk Protein (*lactis* Proteinum) by weight;
g. approximately 1-4% Panthenyl Ethyl Ether by weight;
h. approximately 1-4% Sodium Citrate by weight;
i. approximately 4-20% Acrylates/C10-30 Alkyl Acrylates Crosspolymer;
j. approximately 1-15% Amodimethicone by weight;
k. approximately 1-15% C11-15 Pareth-7 by weight;
l. approximately 1-15% Laureth-9 by weight;
m. approximately 1-15% Trideceth-12 Paraben-free by weight;
n. approximately 0.5-6% Apigenin by weight;
o. approximately 0.5-6% Biotinoyl Tripeptide by weight;
p. approximately 0.5-6% Butylene Glycol by weight;
q. approximately 0.5-6% Oleanolic Acid by weight;
r. approximately 0.5-6% PEG-40 Hydrogenated Castor Oil by weight
s. approximately 0.5-6% PPG-26-Buteth-26 by weight;
t. approximately 0.5-3% Arginine;
u. approximately 0.5-3% *Glycine soja* (soybean) Germ Extract by weight;
v. approximately 0.5-3% Lactic Acid by weight;
w. approximately 0.5-3% Propanediol by weight;
x. approximately 0.5-3% *Scutellaria ba-icalensis* Root Extract by weight;
y. approximately 0.5-3% *Triticum vulgare* (wheat) Germ Extract by weight;
z. approximately 0.1-4% Beeswax by weight;
aa. approximately 0.1-4% Behenyl Alcohol by weight;
bb. approximately 0.1-4% *Butyrospermum parkii* (Shea Butter) Extract by weight;
cc. approximately 0.1-4% Ethylhexylglycerin by weight;
dd. approximately 0.1-4% Hydroxyethyl Behenamidopropyl Dimonium Chloride by weight;
ee. approximately 0.1-4% Phenoxyethanol by weight;
ff. approximately 0.1-4% *Pyrus malus* Extract by weight;
gg. approximately 0.005-3% *Camellia sinensis* Leaf Extract by weight;
hh. approximately 0.005-3% Caprylic/Capric Triglyceride by weight;
ii. approximately 0.005-3% *Coffea arabica* (Coffee) Leaf/Seed Extract by weight;
jj. approximately 0.005-3% *Cucumis melo* Cantalupensis Fruit Extract by weight;
kk. approximately 0.005-3% *Eugenia caryophyllus* (Clove) Flower Extract by weight;
ll. approximately 0.005-3% *Elettaria cardamomum* Seed Extract by weight;
mm. approximately 0.005-3% *Jasminum officinale* (Jasmine) Flower/Leaf Extract (and) *Pyrus malus* Apple Fruit Extract by weight;
nn. approximately 0.005-3% *Rosa damascena* Flower Extract by weight;
oo. approximately 0.005-3% *Rubus fruticosus* (Blackberry) Fruit Extract by weight;
pp. approximately 0.005-4% Caprylhydroxamic Acid by weight;
qq. approximately 0.005-4% Caprylyl Glycol by weight;
rr. approximately 2-12% Cetyl Betaine by weight;
ss. approximately 0.001-4% Citric Acid by weight;
tt. approximately 0.0001-7% *Citrullus colocynthis* Fruit Extract by weight;
uu. approximately 0.0001-7% *Pisum sativum* (Pea) Peptide by weight;
vv. approximately 0.0001-7% *Serenoa* by weight;
ww. approximately 1-5% Cocamidopropyl Betaine by weight;
xx. approximately 1-5% Glycol Distearate by weight;
yy. approximately 1-5% Laureth-4 by weight;
zz. approximately 18-41% Cocamidopropyl Betaine by weight;
aaa. approximately 18-41% Sodium Cocoyl Isethionate by weight;
bbb. approximately 18-41% Sodium Lauroyl Methyl Isethionate by weight;
ccc. approximately 18-41% Sodium by weight;
ddd. approximately 18-41% Methyl Oleoyl Taurate by weight;
eee. approximately 0.1-3% *Cuscuta reflexa* (Giant Dodder) Extract (and) *Eclipta alba* Extract by weight;
fff. approximately 0.1-15% Glycerin by weight;
ggg. approximately 0.01-3% Guar Hydroxypropyltrimonium Chloride by weight;
hhh. approximately 1-5% Hydrolyzed *quinoa* by weight;
iii. approximately 0.01-5% Hydrolyzed Rice Protein by weight;
jjj. approximately 0.0001-7% *Leuconostoc*/Radish Root Ferment Filtrate by weight;
kkk. approximately 0.0001-7% *serrulata* Fruit Extract by weight;
lll. approximately 0.1-4% Panthenyl Hydroxypropyl Steardimonium Chloride by weight;
mmm. approximately 1-4% Polyquatemium 7 by weight;
nnn. approximately 1-60% Purified Water by weight;
ooo. approximately 0.5-3% Stearamidopropyl Dimethylamine by weight.

The composition in the form of a conditioner comprises or consisting essentially of and can include the following ranges by percent by weight of each ingredient. The composition in the form of a conditioner can also include an alternate embodiment of ranges disclosed below:
a. Amodimethicone;
b. C11-15 Pareth-7;
c. Laureth-9;
d. Glycerin;
e. Trideceth-12;
f. Behentrimonium methosulfate;
g. C10-40 isoalkylamidopropylethyldimonium ethosulfate;
h. cetyl alcohol
i. Butylene Glycol;
j. PPG-26-Buteth-26;
k. PEG-40 Hydrogenated Castor Oil;
l. Apigenin;
m. Oleanolic Acid;
n. Biotinoyl Tripeptide;
o. *Butyrospermum parkii* (Shea Butter);
p. Caprylyl Glycol;
q. Caprylhydroxamic Acid;
r. Cetearyl Alcohol;
s. Cetyl esters;
t. *Citrullus colocynthis* Fruit Extract;
u. *Pisum sativum* (Pea) Peptide;
v. *Serenoa;*
w. *Cocos nucifera* (Coconut) Fruit Extract;
x. Di-PPG-2 Myreth-10 Adipate;
y. PPG-3 Benzyl Ether Myristate;
z. Panthenyl Hydroxypropyl Steardimonium Chloride;
aa. Propanediol;
bb. arginine;
cc. lactic acid;

dd. *Glycine soja* (soybean) germ extract;
ee. *Triticum vulgare* (wheat) germ extract;
ff. *Scutellaria ba-icalensis* root extract;
gg. Purified Water;
hh. Alcohol;
ii. Panthenyl Ethyl Ether;
jj. Inositol;
kk. Milk Protein (*lactis* Proteinum);
ll. Lactose;
mm. Acetyl Cysteine;
nn. Acetyl Methione;
oo. Sodium Citrate;
pp. Citric acid.

The composition in conditioner form having the following ranges:
a. approximately 1-15% Amodimethicone by weight;
b. approximately 1-15% C11-15 Pareth-7 by weight;
c. approximately 1-15% Laureth-9 by weight;
d. approximately 0.005-15% Glycerin by weight;
e. approximately 1-15% Trideceth-12 by weight;
f. approximately 3-15% Behentrimonium methosulfate by weight;
g. approximately 3-15% C10-40 isoalkylamidopropylethyldimonium ethosulfate by weight;
h. approximately 3-15% cetyl alcohol by weight;
i. approximately 0.005-8% Butylene Glycol;
j. approximately 0.005-8% PPG-26-Buteth-26 by weight;
k. approximately 0.005-8% PEG-40 Hydrogenated Castor Oil by weight;
l. approximately 0.005-8% Apigenin by weight;
m. approximately 0.005-8% Oleanolic Acid by weight;
n. approximately 0.005-8% Biotinoyl Tripeptide by weight;
o. approximately 0.05-10% *Butyrospermum parkii* (Shea Butter) by weight;
p. approximately 0.005-8% Caprylyl Glycol by weight;
q. approximately 0.005-8% Caprylhydroxamic Acid by weight;
r. approximately 1-15% Cetearyl Alcohol by weight;
s. approximately 0.0001-4% Cetyl esters by weight;
t. approximately 0.0001-7% *Citrullus colocynthis* Fruit Extract by weight;
u. approximately 0.0001-7% *Pisum sativum* (Pea) Peptide by weight;
v. approximately 0.0001-7% *Serenoa* by weight;
w. approximately 1-12% *Cocos nucifera* (Coconut) Fruit Extract by weight;
x. approximately 1-10% Di-PPG-2 Myreth-10 Adipate by weight;
y. approximately 2-18% PPG-3 Benzyl Ether Myristate by weight;
z. approximately 0.001-8% Panthenyl Hydroxypropyl Steardimonium Chloride by weight;
aa. approximately 0.15-8% Propanediol by weight;
bb. approximately 0.15-8% arginine by weight;
cc. approximately 0.15-8% lactic acid by weight;
dd. approximately 0.15-8% *Glycine soja* (soybean) germ extract by weight;
ee. approximately 0.15-8% *Triticum vulgare* (wheat) germ extract by weight;
ff. approximately 0.15-8% *Scutellaria ba-icalensis* root extract by weight;
gg. approximately 1-60% Purified Water by weight; and
hh. approximately 0.0001-17% Alcohol by weight;
ii. approximately 0.0001-17% Panthenyl Ethyl Ether by weight;
jj. approximately 0.0001-17% Inositol by weight;
kk. approximately 0.0001-17% Milk Protein (*lactis* Proteinum) by weight;
ll. approximately 0.0001-17% Lactose by weight;
mm. approximately 0.0001-17% Acetyl Cysteine by weight;
nn. approximately 0.0001-17% Acetyl Methione by weight;
oo. approximately 0.0001-17% Sodium Citrate by weight;
pp. approximately 0.0001-17% Citric acid by weight.

The conditioner having the following ranges in an alternate embodiment:
a. approximately 1-5% Amodimethicone by weight;
b. approximately 1-5% C11-15 Pareth-7 by weight;
c. approximately 1-5% Laureth-9 by weight;
d. approximately 1-5% Glycerin by weight;
e. approximately 1-5% Trideceth-12 by weight;
f. approximately 1-10% Behentrimonium methosulfate by weight;
g. approximately 1-10% C10-40 isoalkylamidopropylethyldimonium ethosulfate by weight;
h. approximately 1-10% cetyl alcohol by weight;
i. approximately 0.05-4% Butylene Glycol by weight;
j. approximately 0.05-4% PPG-26-Buteth-26 by weight;
k. approximately 0.05-4% PEG-40 Hydrogenated Castor Oil by weight;
l. approximately 0.05-4% Apigenin by weight;
m. approximately 0.05-4% Oleanolic Acid by weight;
n. approximately 0.05-4% Biotinoyl Tripeptide by weight;
o. approximately 0.05-4% *Butyrospermum parkii* (Shea Butter) by weight;
p. approximately 0.005-3% Caprylyl Glycol by weight;
q. approximately 0.005-3% Caprylhydroxamic Acid by weight;
r. approximately 1-6% Cetearyl Alcohol by weight;
s. approximately 0.0001-4% Cetyl esters by weight;
t. approximately 0.1-4% *Citrullus colocynthis* Fruit Extract by weight;
u. approximately 0.1-4% *Pisum sativum* (Pea) Peptide by weight;
v. approximately 0.1-4% *Serenoa* by weight;
w. approximately 1-8% *Cocos nucifera* (Coconut) Fruit Extract by weight;
x. approximately 1-5% Di-PPG-2 Myreth-10 Adipate by weight;
z. approximately 2-18% PPG-3 Benzyl Ether Myristate by weight;
aa. approximately 0.01-4% Panthenyl Hydroxypropyl Steardimonium Chloride by weight;
bb. approximately 0.15-4% Propanediol by weight;
cc. approximately 0.15-4% arginine by weight;
dd. approximately 0.15-4% lactic acid by weight;
ee. approximately 0.15-4% *Glycine soja* (soybean) germ extract by weight;
ff. approximately 0.15-4% *Triticum vulgare* (wheat) germ extract by weight;
gg. approximately 0.15-4% *Scutellaria ba-icalensis* root extract by weight;
hh. approximately 1-50% Purified Water by weight;
ii. approximately 0.005-4% Alcohol by weight;
jj. approximately 0.005-4% Panthenyl Ethyl Ether by weight;
kk. approximately 0.005-4% Inositol by weight;
ll. approximately 0.005-4% Milk Protein (*lactis* Proteinum) by weight;
mm. approximately 0.005-4% Lactose by weight;
nn. approximately 0.005-4% Acetyl Cysteine by weight;

oo. approximately 0.005-4% Acetyl Methione by weight;
pp. approximately 0.005-4% Sodium Citrate weight;
qq. approximately 0.005-4% Citric acid by weight.

The composition in the form of a serum comprising or consisting essentially of the following ingredients in the following ranges. Below are some examples of ingredients along with their functions.

Butylene Glycol (and) Water (and) PPG-26-Buteth-26 (and) PEG-40 Hydrogenated Castor Oil Oleanolic Acid (and) Biotinoyl Tripeptide facilitates the communication of cells and holds them together. *Citrullus colocynthis* Fruit Extract (and) *Pisum sativum* (Pea) Peptide to stimulate hair follicles;

Emu oil. Provides Nourishing/Moisturizing Properties and helps the hair look shinier;

Panthenol. Topical application of panthenol and other forms of vitamin B5 to increase healing and suppress free radical formation on skin/scalp and it helps increase the skin/scalp barrier function, helping to repair and prevent damage from UV rays. Helps the hair look shinier;

Polyglyceryl-10 stearate. Emulsifier.

a. Acacia Senegal Gum;
b. Xanthan Gum;
c. *Argania spinosa* Kernel Oil;
d. Butylene Glycol;
e. PPG-26-Buteth-26;
f. PEG-40 Hydrogenated Castor Oil;
g. Apigenin;
h. Oleanolic Acid;
i. Biotinoyl Tripeptide;
j. *Cananga odorata* Flower Extract
k. Caprylic/Capric Triglyceride;
l. *Jasminum officinale* (Jasmine) Flower/Leaf Extract;
m. *Pyrus malus* (Apple) Fruit Extract;
n. *Camellia sinensis* Leaf Extract;
o. *Coffea arabica* (Coffee) Leaf/Seed Extract;
p. *Cucumis melo* (melon) Fruit Extract;
q. Rose Extract;
r. *Eugenia caryophyllus* (Clove) Flower Extract;
s. *Prunus armeniaca* (Apricot) Fruit Extract;
t. *Cucumis melo* Cantalupensis Fruit Extract;
u. *Rubus idaeus* (Raspberry) Fruit Extract;
v. *Lavandula angustifolia* (Lavender) Flower/Leaf/Stem Extract;
w. *Vitis vinifera* (Grape) Fruit Extract;
x. *Impatiens balsamina* Flower Extract;
y. *Citrus aurantium dulcis* (Orange) Peel Extract;
z. *Hibiscus sabdariffa* Flower Extract;
aa. Caprylyl Glycol;
bb. Caprylhydroxamic Acid;
cc. Glycerin;
dd. *Citrullus colocynthis* Fruit Extract;
ee. *Pisum sativum* (Pea) Peptide;
ff. *Serenoa;*
gg. Emu oil;
hh. *Cuscuta reflexa* (Giant Dodder) Extract;
ii. *Eclipta alba* Extract;
jj. *Camellis sinensis* Leaf (Green Tea) Extract;
kk. *Helianthus annuus* (Sunflower) Seed Oil;
ll. *Hyacinthus orientalis* (Hyacinth) Flower Extract;
mm. *Citrus tangerina* (Tangerine) Peel Extract;
nn. Panthenol;
oo. *Pisum sativum* (Pea) Sprout Extract;
pp. Phenoxyethanol;
qq. Sodium Benzoate;
rr. Polyglyceryl-10 stearate;
ss. Propanediol;
tt. Purified water;
uu. Raspberry Ketone;
vv. *serrulata* Fruit Extract;
ww. *Leuconostoc*/Radish Root Ferment Filtrate;
xx. Hydrolyzed Rice Protein; and
yy. Hexylene Glycol;
zz. Betaine;
aaa. Superoxide Dismutase;
bbb. *Foeniculum vulgare* (Fennel) Seed Extract;
ccc. *Visnaga vera* Fruit/Stem Extract.

An anti-aging composition in serum form can be implemented in the following ranges:

a. approximately 0.1-7% Acacia Senegal Gum by weight;
b. approximately 0.1-7% Xanthan Gum by weight;
c. approximately 0.1-10% *Argania spinosa* Kernel Oil by weight;
d. approximately 0.5-9% Butylene Glycol by weight;
e. approximately 0.5-9% PPG-26-Buteth-26 by weight;
f. approximately 0.5-9% PEG-40 Hydrogenated Castor Oil by weight;
g. approximately 0.5-9% Apigenin by weight;
h. approximately 0.5-9% Oleanolic Acid by weight;
i. approximately 0.5-9% Biotinoyl Tripeptide by weight;
j. approximately 0.2-5% *Cananga odorata* Flower Extract by weight
k. approximately 0.2-5% Caprylic/Capric Triglyceride by weight;
l. approximately 0.2-5% *Jasminum officinale* (Jasmine) Flower/Leaf Extract by weight;
m. approximately 0.2-5% *Pyrus malus* (Apple) Fruit Extract by weight;
n. approximately 0.2-5% *Camellia sinensis* Leaf Extract by weight;
o. approximately 0.2-5% *Coffea arabica* (Coffee) Leaf/Seed Extract by weight;
p. approximately 0.2-5% *Cucumis melo* (melon) Fruit Extract by weight;
q. approximately 0.2-5% Rose Extract by weight;
r. approximately 0.2-5% *Eugenia caryophyllus* (Clove) Flower Extract by weight;
s. approximately 0.2-5% *Prunus armeniaca* (Apricot) Fruit Extract by weight;
t. approximately 0.2-5% *Cucumis melo* Cantalupensis Fruit Extract by weight;
u. approximately 0.2-5% *Rubus idaeus* (Raspberry) Fruit Extract by weight;
v. approximately 0.2-5% *Lavandula angustifolia* (Lavender) Flower/Leaf/Stem Extract by weight;
w. approximately 0.2-5% *Vitis vinifera* (Grape) Fruit Extract by weight;
x. approximately 0.2-5% *Impatiens balsamina* Flower Extract by weight;
y. approximately 0.2-5% *Citrus aurantium dulcis* (Orange) Peel Extract by weight;
z. approximately 0.2-5% *Hibiscus sabdariffa* Flower Extract by weight;
aa. approximately 0.5-12% Caprylyl Glycol by weight;
bb. approximately 0.5-12% Caprylhydroxamic Acid by weight;
cc. approximately 0.1-12% Glycerin by weight;
dd. approximately 1-40% *Citrullus colocynthis* Fruit Extract by weight;
ee. approximately 1-40% *Pisum sativum* (Pea) Peptide by weight;
ff. approximately 1-40% *Serenoa* by weight;
gg. approximately 1-40% Emu oil by weight;

hh. approximately 1-40% *Cuscuta reflexa* (Giant Dodder) Extract by weight;
ii. approximately 1-40% *Eclipta alba* Extract by weight;
jj. approximately 1-10% *Camellis sinensis* Leaf (Green Tea) Extract by weight;
kk. approximately 0.2-5% *Helianthus annuus* (Sunflower) Seed Oil by weight;
ll. approximately 0.2-5% *Hyacinthus orientalis* (Hyacinth) Flower Extract by weight;
mm. approximately 0.2-5% *Citrus tangerina* (Tangerine) Peel Extract by weight;
nn. approximately 0.3-6% Panthenol by weight;
oo. approximately 0.5-10% *Pisum sativum* (Pea) Sprout Extract by weight;
pp. approximately 0.5-10% Phenoxyethanol by weight;
qq. approximately 0.5-10% Sodium Benzoate by weight;
rr. approximately 1-10% Polyglyceryl-10 stearate by weight;
ss. approximately 0.01-5% Propanediol by weight;
tt. approximately 1-60% Purified water by weight;
uu. approximately 0.15-5% Raspberry Ketone by weight;
vv. approximately 1-40% *serrulata* Fruit Extract by weight;
ww. approximately 1-40% *Leuconostoc*/Radish Root Ferment Filtrate by weight;
xx. approximately 0.1-10% Hydrolyzed Rice Protein by weight;
yy. approximately 1-10% Hexylene Glycol by weight;
zz. approximately 1-10% Betaine by weight;
aaa. approximately 1-10% Superoxide Dismutase by weight;
bbb. approximately 1-10% *Foeniculum vulgare* (Fennel) Seed Extract by weight; and
ccc. approximately 1-10% *Visnaga vera* Fruit/Stem Extract by weight.

The anti-aging hair composition in serum form can be implemented in the following ranges:
a. approximately 0.3-4% Acacia Senegal Gum by weight;
b. approximately 0.3-4% Xanthan Gum by weight;
c. approximately 0.1-3% *Argania spinosa* Kernel Oil by weight;
d. approximately 1-8% Betaine by weight;
e. approximately 1-5% Butylene Glycol by weight;
f. approximately 1-5% Apigenin by weight;
g. approximately 1-5% Oleanolic Acid by weight;
h. approximately 1-5% Biotinoyl Tripeptide by weight;
i. approximately 0.1-3% *Cananga odorata* Flower Extract by weight
j. approximately 0.1-3% Caprylic/Capric Triglyceride by weight;
k. approximately 0.1-3% *Jasminum officinale* (Jasmine) Flower/Leaf Extract by weight;
l. approximately 0.1-3% *Pyrus malus* (Apple) Fruit Extract by weight;
m. approximately 0.1-3% *Camellia sinensis* Leaf Extract by weight;
n. approximately 0.1-3% *Coffea arabica* (Coffee) Leaf/Seed Extract by weight;
o. approximately 0.1-3% *Cucumis melo* (melon) Fruit Extract by weight;
p. approximately 0.1-3% Rose Extract by weight;
q. approximately 0.1-3% *Eugenia caryophyllus* (Clove) Flower Extract by weight;
r. approximately 0.1-3% *Cucumis melo* Cantalupensis Fruit Extract by weight;
s. approximately 0.1-3% *Lavandula angustifolia* (Lavender) Flower/Leaf/Stem Extract by weight;
t. approximately 0.1-3% *Vitis vinifera* (Grape) Fruit Extract by weight;
u. approximately 0.1-3% *Impatiens balsamina* Flower Extract by weight;
v. approximately 0.5-8% Caprylyl Glycol by weight;
w. approximately 0.5-8% Caprylhydroxamic Acid by weight;
x. approximately 1-5% *Camellis sinensis* Leaf (Green Tea) Extract by weight;
y. approximately 1-15% *Citrullus colocynthis* Fruit Extract by weight;
z. approximately 0.1-3% *Citrus aurantium dulcis* (Orange) Peel Extract by weight;
aa. approximately 0.1-3% *Citrus tangerina* (Tangerine) Peel Extract by weight;
bb. approximately 1-15% *Cuscuta reflexa* (Giant Dodder) Extract by weight;
cc. approximately 1-15% *Eclipta alba* Extract by weight;
dd. approximately 0.25-10% Emu oil by weight;
ee. approximately 1-8% *Foeniculum vulgare* (Fennel) Seed Extract by weight; and
ff. approximately 0.5-8% Glycerin by weight;
gg. approximately 0.1-3% *Helianthus annuus* (Sunflower) Seed Oil by weight;
hh. approximately 0.1-3% *Hibiscus sabdariffa* Flower Extract by weight;
ii. approximately 0.1-3% *Hyacinthus orientalis* (Hyacinth) Flower Extract by weight;
jj. approximately 1-8% Hexylene Glycol by weight;
kk. approximately 0.1-5% Hydrolyzed Rice Protein by weight;
ll. approximately 1-15% *Leuconostoc*/Radish Root Ferment Filtrate by weight;
mm. approximately 0.1-4% Panthenol by weight;
nn. approximately 1-8% Phenoxyethanol by weight;
oo. approximately 1-8% *Pisum sativum* (Pea) Sprout Extract by weight;
pp. approximately 1-8% *Pisum sativum* (Pea) Peptide by weight;
qq. approximately 1-5% Polyglyceryl-10 stearate by weight;
rr. approximately 1-5% PEG-40 Hydrogenated Castor Oil by weight;
ss. approximately 1-5% PPG-26-Buteth-26 by weight;
tt. approximately 0.25-3% Propanediol by weight;
uu. approximately 0.1-3% *Prunus armeniaca* (Apricot) Fruit Extract by weight;
vv. approximately 1-60% Purified water by weight;
ww. approximately 0.2-3% Raspberry Ketone by weight;
xx. approximately 0.1-3% *Rubus idaeus* (Raspberry) Fruit Extract by weight;
yy. approximately 1-15% *Serenoa* by weight;
zz. approximately 1-15% *serrulata* Fruit Extract by weight;
aaa. approximately 1-8% Sodium Benzoate by weight;
bbb. approximately 1-8% Superoxide Dismutase by weight;
ccc. approximately 1-8% *Visnaga vera* Fruit/Stem Extract by weight.

Application of Composition:
Shampoo
Apply on scalp in a circular motion at the hair root and leave on for five minutes or longer. Can be used as desired, for optimal results use 3-5× a week.

Conditioner

Apply on scalp in a circular motion at the hair root and leave on for five minutes or longer. Can be used as desired, for optimal results use 3-5× a week.

Serum

Apply on top of scalp at the hair root in a circular motion onto the ends of the hair. Can be applied up to twice a day and can be applied to the scalp and eyebrows.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An anti-aging composition in conditioner form comprising:
   a. Amodimethicone;
   b. C 11-15 Pareth-7;
   c. Laureth-9;
   d. Glycerin;
   e. Trideceth-12;
   f. Behentrimonium methosulfate;
   g. C10-40 isoalkylamidopropylethyldimonium ethosulfate;
   h. cetyl alcohol
   I. Butylene Glycol;
   j. PPG-26-Buteth-26;
   k. PEG-40 Hydrogenated Castor Oil; 1. Apigenin;
   m. Oleanolic Acid;
   n. Biotinoyl Tripeptide;
   o. *Butyrospermum parkii* (Shea Butter);
   p. Caprylyl Glycol;
   q. Caprylhydroxamic Acid;
   r. Cetearyl Alcohol;
   s. Cetyl esters;
   t. *Citrullus colocynthis* Fruit Extract;
   u. *Pisum sativum* (Pea) Peptide;
   v. *Serenoa*;
   w. *Cocos Nucifera* (Coconut) Fruit Extract;
   x. Di-PPG-2 Myreth-10 Adipate;
   y. PPG-3 Benzyl Ether Myristate;
   z. Panthenyl Hydroxypropyl Steardimonium Chloride;
   aa. Propanediol;
   bb. arginine;
   cc. lactic acid;
   dd. *Glycine soja* (soybean) germ extract;
   ee. *Triticum vulgare* (wheat) germ extract;
   ff. *Scutellaria ba-icalensis* root extract;
   gg. Purified Water;
   hh. Alcohol;
   ii. Panthenyl Ethyl Ether;
   jj. Inositol;
   kk. Milk Protein (*lactis* Proteinum);
   ll. Lactose;
   mm. Acetyl Cysteine;
   nn. Acetyl Methione;
   oo. Sodium Citrate;
   pp. Citric acid.

2. The composition of claim 1 comprising:
   a. approximately 1-15% Amodimethicone by weight;
   b. approximately 1-15% C 11-15 Pareth-7 by weight;
   c. approximately 1-15% Laureth-9 by weight;
   d. approximately 0.005-15% Glycerin by weight;
   e. approximately 1-15% Trideceth-12 by weight;
   f. approximately 3-15% Behentrimonium methosulfate by weight;
   g. approximately 3-15% C 10-40 isoalkylamidopropylethyldimonium ethosulfate by weight;
   h. approximately 3-15% cetyl alcohol by weight;
   i. approximately 0.005-8% Butylene Glycol;
   j. approximately 0.005-8% PPG-26-Buteth-26 by weight;
   k. approximately 0.005-8% PEG-40 Hydrogenated Castor Oil by weight;
   l. approximately 0.005-8% Apigenin by weight;
   m. approximately 0.005-8% Oleanolic Acid by weight;
   n. approximately 0.005-8% Biotinoyl Tripeptide by weight;
   o. approximately 0.05-10% *Butyrospermum parkii* (Shea Butter) by weight;
   p. approximately 0.005-8% Caprylyl Glycol by weight;
   q. approximately 0.005-8% Caprylhydroxamic Acid by weight;
   r. approximately 1-15% Cetearyl Alcohol by weight;
   s. approximately 0.0001-4% Cetyl esters by weight;
   t. approximately 0.0001-7% *Citrullus colocynthis* Fruit Extract by weight;
   u. approximately 0.0001-7% *Pisum sativum* (Pea) Peptide by weight;
   v. approximately 0.0001-7% *Serenoa* by weight;
   w. approximately 1-12% *Cocos nucifera* (Coconut) Fruit Extract by weight;
   x. approximately 1-10% Di-PPG-2 Myreth-10 Adipate by weight;
   y. approximately 2-18% PPG-3 Benzyl Ether Myristate by weight;
   z. approximately 0.001-8% Panthenyl Hydroxypropyl Steardimonium Chloride by weight;
   aa. approximately 0.15-8% Propanediol by weight;
   bb. approximately 0.15-8% arginine by weight;
   cc. approximately 0.15-8% lactic acid by weight;
   dd. approximately 0.15-8% *Glycine soja* (soybean) germ extract by weight;
   ee. approximately 0.15-8% *Triticum vulgare* (wheat) germ extract by weight;
   ff. approximately 0.15-8% *Scutellaria ba-icalensis* root extract by weight;
   gg. approximately 1-60% Purified Water by weight; and
   hh. approximately 0.0001-17% Alcohol by weight;
   ii. approximately 0.0001-17% Panthenyl Ethyl Ether by weight;
   jj. approximately 0.0001-17% Inositol by weight;
   kk. approximately 0.0001-17% Milk Protein (*lactis* Proteinum) by weight;
   ll. approximately 0.0001-17% Lactose by weight;
   mm. approximately 0.0001-17% Acetyl Cysteine by weight;
   nn. approximately 0.0001-17% Acetyl Methione by weight;
   oo. approximately 0.0001-17% Sodium Citrate by weight;
   pp. approximately 0.0001-17% Citric acid by weight.

3. The composition of claim 1 including:
   a. approximately 1-5% Amodimethicone by weight;
   b. approximately 1-5% C 11-15 Pareth-7 by weight;
   c. approximately 1-5% Laureth-9 by weight;
   d. approximately 1-5% Glycerin by weight;
   e. approximately 1-5% Trideceth-12 by weight;
   f. approximately 1-10% Behentrimonium methosulfate by weight;
   g. approximately 1-10% C 10-40 isoalkylamidopropylethyldimonium ethosulfate by weight;
   h. approximately 1-10% cetyl alcohol by weight;
   i. approximately 0.05-4% Butylene Glycol by weight;
   j. approximately 0.05-4% PPG-26-Buteth-26 by weight;

k. approximately 0.05-4% PEG-40 Hydrogenated Castor Oil by weight;
l. approximately 0.05-4% Apigenin by weight;
m. approximately 0.05-4% Oleanolic Acid by weight;
n. approximately 0.05-4% Biotinoyl Tripeptide by weight;
o. approximately 0.05-4% *Butyrospermum parkii* (Shea Butter) by weight;
p. approximately 0.005-3% Caprylyl Glycol by weight;
q. approximately 0.005-3% Caprylhydroxamic Acid by weight;
r. approximately 1-6% Cetearyl Alcohol by weight;
s. approximately 0.0001-4% Cetyl esters by weight;
t. approximately 0.1-4% *Citrullus colocynthis* Fruit Extract by weight;
u. approximately 0.1-4% *Pisum sativum* (Pea) Peptide by weight;
v. approximately 0.1-4% *Serenoa* by weight;
w. approximately 1-8% *Cocos nucifera* (Coconut) Fruit Extract by weight;
x. approximately 1-5% Di-PPG-2 Myreth-10 Adipate by weight;
y. approximately 2-18% PPG-3 Benzyl Ether Myristate by weight;
z. approximately 0.01-4% Panthenyl Hydroxypropyl Steardimonium Chloride by weight;
aa. approximately 0.15-4% Propanediol by weight;
bb. approximately 0.15-4% arginine by weight;
cc. approximately 0.15-4% lactic acid by weight;
dd. approximately 0.15-4% *Glycine soja* (soybean) germ extract by weight;
ee. approximately 0.15-4% *Triticum vulgare* (wheat) germ extract by weight;
ff. approximately 0.15-4% *Scutellaria ba-icalensis* root extract by weight;
gg. approximately 1-50% Purified Water by weight;
hh. approximately 0.005-4% Alcohol by weight;
ii. approximately 0.005-4% Panthenyl Ethyl Ether by weight;
jj. approximately 0.005-4% Inositol by weight;
kk. approximately 0.005-4% Milk Protein (*lactis* Proteinum) by weight; ll. approximately 0.005-4% Lactose by weight;
mm. approximately 0.005-4% Acetyl Cysteine by weight;
nn. approximately 0.005-4% Acetyl Methione by weight;
oo. approximately 0.005-4% Sodium Citrate weight;
pp. approximately 0.005-4% Citric acid by weight.

\* \* \* \* \*